United States Patent [19]

Heinz

[11] 4,256,966
[45] Mar. 17, 1981

[54] RADIOTHERAPY APPARATUS WITH TWO LIGHT BEAM LOCALIZERS

[75] Inventor: Lothar R. Heinz, Lafayette, Calif.

[73] Assignee: Siemens Medical Laboratories, Inc., Walnut Creek, Calif.

[21] Appl. No.: 69,294

[22] Filed: Aug. 24, 1979

[30] Foreign Application Priority Data

Jul. 3, 1979 [DE] Fed. Rep. of Germany ....... 2926873

[51] Int. Cl.³ ..................... G01N 21/00; G01N 23/00
[52] U.S. Cl. ................................. 250/491; 250/492 B
[58] Field of Search ........... 250/454, 523, 491, 492 R, 250/492 B

[56] References Cited

U.S. PATENT DOCUMENTS

| | | | |
|---|---|---|---|
| 2,204,465 | 6/1940 | Baier | 250/491 |
| 2,474,422 | 5/1959 | Reininger | 250/493 |
| 2,887,586 | 5/1959 | Reininger | 250/491 |
| 3,757,118 | 9/1973 | Hodge | 250/491 |
| 4,123,660 | 10/1978 | Horwitz | 250/491 |
| 4,132,900 | 1/1979 | Smith et al. | 250/491 |

*Primary Examiner*—Bruce C. Anderson
*Attorney, Agent, or Firm*—Spellman, Joel & Pelton

[57] ABSTRACT

The radiation emitting apparatus contains a radiation source which projects a beam of radiation along a central axis onto a surface to be irradiated. There are provided a first and a second light-beam localizer for emitting a first and a second plane light fan, respectively, towards the surface to be irradiated. The second light fan intersects the first light fan in an intersecting line which coincides with the central axis of the emitted radiation. A scale may be projected towards the surface along with one of the light fans. In a preferred embodiment the radiation source is an electron accelerator and the surface is the skin of a patient to be treated.

5 Claims, 4 Drawing Figures

RADIOTHERAPY APPARATUS WITH TWO LIGHT BEAM LOCALIZERS

BACKGROUND OF THE INVENTION

1. Field of the Invention

This invention relates in general to a novel and improved apparatus which emits radiation, preferably for treating patients. In particular, it relates to a novel and improved apparatus for radiation therapy, preferably with accelerated electrons. More particularly, this invention is directed to a radiotherapy apparatus having light beam localizers for the projection of light beams on the surface of a body to be subjected to irradiation in order to determine the position of that surface.

2. Description of the Prior Art

From U.S. Pat. Nos. 2,204,465; 2,474,422 and 2,887,586 X-ray examination apparatus are known having arranged a mirror in the X-ray cone between the X-ray radiation source and the radiation diaphragm. The mirror is inclined by about 45° to the axis of symmetry of the radiation diaphragm. This mirror projects light of a visible light source, which is arranged laterally of the mirror, through the aperture of the primary radiation diaphragm onto the surface of the object to be examined. The cone of visible light is bonded in the same manner by the diaphragm plates of the primary radiation diaphragm as the X-rays. In these so-called full field light-beam localizers, the visible light source illuminates exactly the same field which would be hit by the X-rays with the X-ray source turned on. These light-beam localizers facilitate considerably the adjustment of the X-ray radiation beam with respect to the skin area of the patient to be examined, because the illuminated field is visible on the skin surface. They are frequently also equipped with a reticle to mark the axis of symmetry of the primary radiation diaphragm on the skin surface.

From U.S. Pat. No. 3,803,418 an X-ray device for examination of skulls is known. A projector is installed in the axis of rotation about which the X-ray examination device may be rotated. A reticular light beam is radiated by the projector along the axis of rotation of the x-ray device. On the skull to be irradiated, the reticle indicates the point which lies on the axis of rotation. Of particular interest in radiation therapy, however, is the determination of the isocenter. In this respect, it is considered a disadvantage that the reticle projected on the skull of a patient is sometimes far away from the center of the disease, which is, for example, in the trunk of the body.

It is also known in radiotherapy apparatus to project a scale onto the skin surface of the patient by means of an additional projector. This scale intersects the reticle of a light-beam localizer of the radiation diaphragm. To this scale are assigned numerical values which indicate the distance of the skin surface from the focus in the intersection of the reticle of the light-beam localizer projected on the skin surface. This very practical indication device for indicating the focus-skin distance, however, can only be used for X-ray examination apparatus and for radiotherapy apparatus which work with X-rays or gamma rays. In radiotherapy apparatus which work with radiation of a lesser penetration, such as accelerated electrons, this device is not suitable, because of the absorption of the deflection mirror of the light-beam localizer which is provided in the path of rays.

SUMMARY OF THE INVENTION

1. Objects

One object of the present invention is to provide a radiation-emitting apparatus, particularly a radiotherapy apparatus, in which the location of the radiation on the area of a body to be irradiated may easily be determined.

Another object of the present invention is to provide a beam-emitting apparatus, particularly a radiotherapy apparatus, in which the location of the central beam on the surface to be treated may easily be determined.

Another object of the present invention is to provide a beam-emitting apparatus, particularly a radiotherapy apparatus, working with less penetrating radiation, e.g. with accelerated electrons, in which the location of the central beam on a surface to be irradiated may easily be determined by the operator.

Another object of the present invention is to provide a beam-emitting apparatus, particularly a radiotherapy apparatus, in which the location of the central beam on a surface to be irradiated can be determined without using any absorbing obstacle in the irradiation path.

Another object of the present invention is to provide a beam-emitting radiotherapy apparatus in which the distance between a surface to be irradiated, particularly the skin surface of a patient, and the focus of the emitted beam is indicated.

Another object of the present invention is to provide a radiotherapy apparatus in which the depth of the isocenter in the body of the patient is indicated.

Another object of the present invention is to provide a beam-emitting apparatus, particularly a radiotherapy apparatus, creating two lines of visible light crosswise on the surface to be subjected to irradiation.

Another object of the present invention is to provide a beam-emitting apparatus, particularly a radiotherapy apparatus, directing two elongated lines of visible light onto the surface to be irradiated, the crossing point of which indicating the axis of the central beam.

Another object of the present invention is to provide a beam-emitting apparatus, particularly a radiotherapy apparatus, directing two visible light lines onto a surface, the light lines being projected from light sources that are movable along with the source of radiation.

Another object of the present invention is to provide a beam-emitting apparatus, particularly a radiotherapy apparatus, that includes an electron accelerator and a U-shaped frame being rotable about a horizontal axis, in which the location of radiation to be emitted on a body to be treated may easily be determined at all positions of the rotable frame.

Another object of the present invention is to provide a radiotherapy apparatus with light-beam localizers for the projection of coordinates on the surface of the object to be treated, the coordinates marking the setting of the apparatus.

Still other objects will become apparent in the course of the following description.

2. Summary

According to the invention, a radiation emitting apparatus comprises a radiation source, a first and a second lightbeam localizer. The radiation source is adapted to project a beam of radiation along a central axis onto the surface to be irradiated. The first and the second light-beam localizers are adapted for emitting a first and a second "plane light fan" towards the surface to be treated. The second light fan intersects the first light fan in an intersecting line which coincides with the central axis of the radiation source.

Preferably a scale is projected towards the surface to be irradiated along with one of the two plane light fans.

The term "plane light fan", as used herein, is intended to define a planar and fan-shaped beam of light; that is, a beam which is substantially planar and extends outwardly with an aperture angle from at least one source.

This apparatus avoids that any part of the light-beam localizers is in the path of rays of the radiotherapy apparatus, and can absorb radiation there. Furthermore the intersection line of the two planes of the light fans coincident with the central axis or the axis of symmetry of the radiation source insures that the axis of symmetry and thus the center ray of the radiation field can be recognized on the surface of the patient. Also, it is possible to use a radiation source the radiation of which is focused at a focal point. By projecting the scale together with one of the light fans, the distance of the radiation focal point from the radiation source can be recognized from the position of the scale relative to the intersection of the two fans with the central axis.

The reading of the focal distance is greatly facilitated if the scale is provided with numerals which indicate in the respective intersection of the two light fans the distance from the focus of the radiation source. The focus-skin distance, which is important for radiation therapy, can thus be read directly in the intersection of the two light lines which are formed by light fans on the skin surface of a patient.

The radiation emitting apparatus may further comprise an axis of rotation about which the source or the object to be radiated may be rotated. Since the distance of the focus from the axis of rotation of the apparatus is usually known, it is only necessary to deduct the numerical value which has been read from the known value of the distance of the focus from the axis of rotation, in order to obtain the depth of the location of the isocenter under the skin surface.

A good readability of the scale is obtained if the light lines of the two light fans projected on a plane extending perpendicularly to the axis of symmetry of the radiotherapy apparatus form with each other an angle of at least 10 degrees, but not more than 170 degrees. In this range the two light fans intersect in a sufficiently large angle so that their intersection can be read with sufficient accuracy.

A particularly useful construction is obtained if the direction of projection of the light-beam localizers forms, over the entire aperture angle of the respective light fan, an angle of at least 20 degrees and not more than 80 degrees with a plane extending perpendicularly to the axis of symmetry. If the angle is selected smaller than 20 degrees, it can happen that the projected light marks are covered by curvatures of the surface of the body to be irradiated. If the angle is selected greater than 80 degrees, the reading accuracy of the scale is too much reduced.

In an advantageous embodiment of the invention, the numerals of the scale can be distorted in the lightbeam localizer in such a way that they are only corrected by the projection on a plane extending perpendicularly to the axis of symmetry. This measure has the advantage that even scale values projected with a flat angle on the skin surface of the patient, which surface is mostly perpendicular to the axis of symmetry, can be read without difficulty.

BRIEF DESCRIPTION OF THE DRAWINGS

The foregoing and other objects, features, and advantages of the invention will be apparent from the following more particular description of a preferred embodiment of the invention.

In the drawings.

DESCRIPTION OF THE PREFERRED EMBODIMENT

Figure 1:
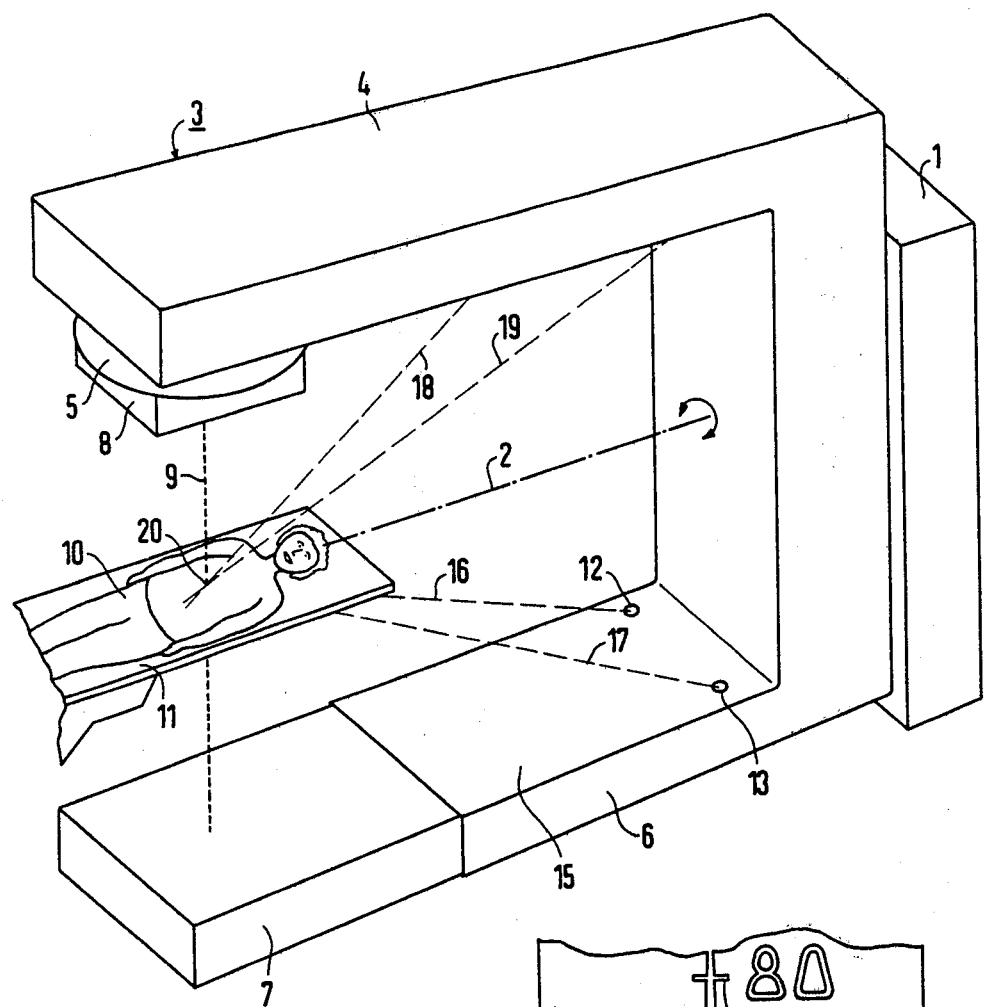
FIG. 1 shows a perspective view of a radiotherapy apparatus using light-beam localizers.

FIG. 1 shows a radiotherapy apparatus 3 secured on a column 1 which is anchored on the floor. The radiotherapy apparatus 3, which may be rotated about a horizontal axis of rotation 2, comprises a substantially U-shaped frame or housing 15, having a base 46 and two horizontal arms 4 and 6. One arm 4 carries a radiation head 5, and the other arm carries a ray trap 7 which can be extended, if required. In the radiator head 5 is arranged, among others, a radiation source (not shown). In the present case, the radiation source is an electron accelerator having an electron exit window to emit electrons. A radiation diaphragm 8 is associated with the radiator head 5. The axis of symmetry 9 of the diaphragm 8, which coincides with the central beam of the emerging radiation field with symmetrical opening, is indicated by a dotted line in the drawing. The axis of symmetry 9 therefore could also be called central beam axis or central axis. It is centered on the ray trap 7 at the end of arm 6, which is shown extended in FIG. 1. An object to be treated or a patient 10 lies on a bearing plate 11 in the range of the radiation field emitted from the radiation source.

On the inner side of each arm 4 and 6 are arranged in the edge zone near the bottom of frame 15 two light beam localizers, which are adapted to emit visible light. In FIG. 1 the two light beam localizers of arm 6 are denoted by numerals 12 and 13. The two light beam localizers of arm 4 cannot be seen in FIG. 1. (In FIG. 3 one of the four light beam localizers will be denoted by reference numeral 14, as will be apparent from the subsequent description). Both sets of light beam localizers are arranged symmetrically with respect to the plane formed by the axis of rotation 2 and the axis of symmetry 9.

According to FIG. 1, the four light beam localizers are installed in or attached to the frame or housing 15 of the radiotherapy apparatus 3. The optical axes 16, 17, 18 and 19 of these four light beam localizers are indicated in FIG. 1 by broken lines. They are aligned with the so-called isocenter 20, that is the intersection of the axis of rotation 2 with the axis of symmetry 9. In the isocenter 20 the axis of symmetry 9 intersects the axis of rotation 2 preferably at 90°. As can be seen from the drawing, in the isocenter 20 the axes 2, 9, 16, 17, 18 and 19 have a common intersection point. The light beam localizers each project a "plane light fan" which intersects the axis of symmetry 9 in its entire width.

Figure 2:
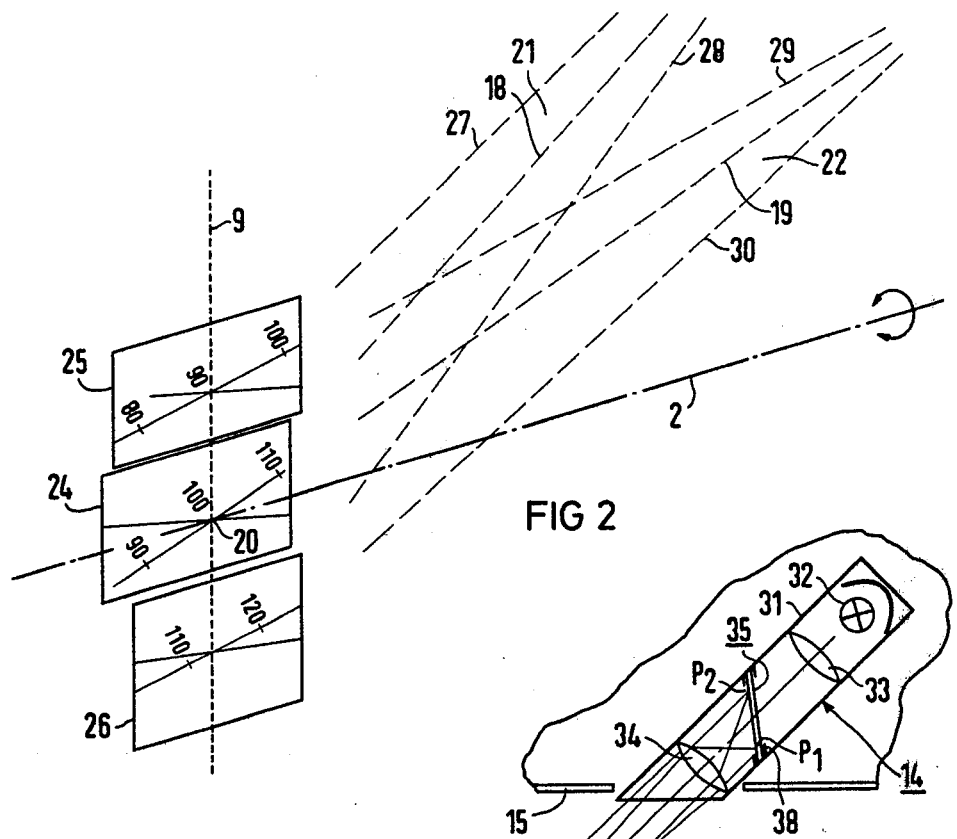
FIG. 2 shows a schematic representation of three parallel surfaces on which are projected coordinates.

FIG. 2 shows as reference coordinates the horizontal axis or rotation 2 (in a dot-dashed line) and the axis of symmetry 9 (in a broken line), which intersect in the isocenter 20. To illustrate the function, a plane 24 extending perpendicularly to the axis of symmetry 9 is drawn through the isocenter 20. Parallel to this plane 24 is shown at each side an additional plane 25 and 26. Also shown in FIG. 2, in broken lines, are the two intersecting plane light fans 21 and 22 of the two light beam localizers associated with the arm 4 of the radiotherapy apparatus 3. The light beam localizers emit each a two-dimensional, i.e. narrow, light fan 21 and 22 which are indicated by broken lines 27, 28, 29 and 30, respectively. The light fans 21 and 22, which are shown to be diverging from their sources over a certain aperture angle, may also be called narrow streaks of visible light rays.

The light fans 21 and 22 traverse each other along the axis of symmetry 9 of radiation diaphragm 8. In other words: The planes of both light fans 21 and 22 intersect in a certain angle, and the intersection line coincides with the axis of symmetry 9. The two light fans 21 and 22 are therefore projected on each of the planes 24, 25 and 26, which extend perpendicularly to the axis of symmetry 9 of the radiation diaphragm 8, as two intersecting light lines. In FIG. 2 these intersecting lines are shown as solid lines in the three planes 24, 25 and 26. The intersection of two intersecting light lines indicates in each plane 24, 25 and 26 the point of impact of the axis of symmetry 9 on the corresponding plane.

Figure 3:
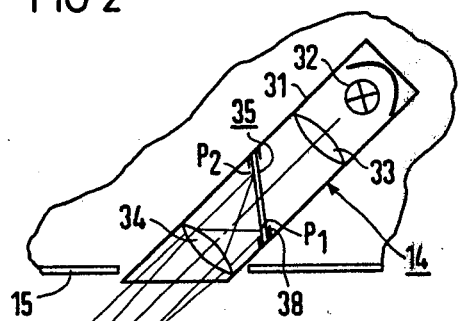
FIG. 3 shows a section through a light-beam localizer and its path of rays.
Figure 3:
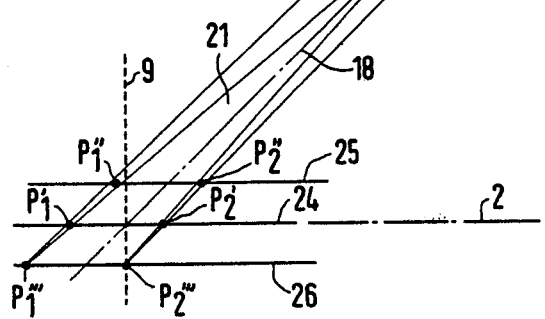

FIG. 3 shows a section through a light-beam localizer 14, which may be one of the light-beam localizers of FIG. 1. It consists of a cylindrical housing 31 with a built-in light source 32 of visible light, a condenser lens 33 arranged in front of the light source 32, and an objective lens 34 arranged at the open end of housing 31 parallel to condenser lens 33. Between condenser lens 33 and objective lens 34 is arranged in an object plane, a template 35 with a slit 36 producing the light fan 29, and with a scale 37 (see FIG. 4) in a slide-in frame 38. The plane of template 35 is turned by the same angle, but in opposite direction to the optical axis 18 of light-beam localizer 14 as the image plane 24 on which the scale 32 is to be produced, that is, a plane extending perpendicularly to the axis of symmetry 9.

Figure 4:
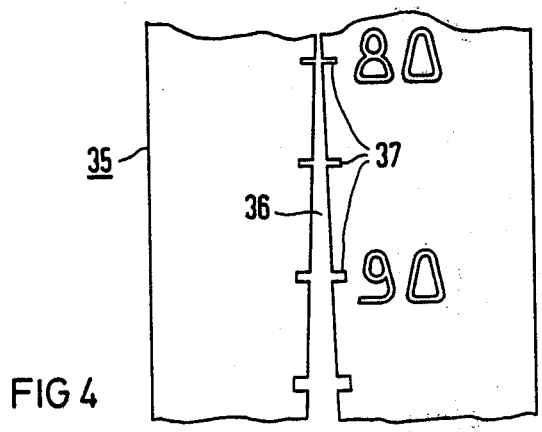
FIG. 4 shows a part of a scale template which may be installed in a light-beam localizer.

FIG. 4 shows a part of template 35 with scale 37 inserted in slide-in frame 38 of light-beam localizer 14. Here the slit 36 responsible for the boundaries of the light fan, some transverse slots producing the divisions of the scale 37, and some numerical data associated with the scale divisions can be seen. All numerals and the scale 37 are distorted in the longitudinal direction of the scale 37 to compensate for the different object-image distance shown in FIG. 3, that is, those parts of the scale 37 and of the numerals which are closer to the image plane 24 are larger, and those which are farther away from the image plane 24 are smaller, so that all numerals are uniformly reproduced in the image plane 24. (In FIG. 4 the lip angle is shown exaggerated). Furthermore, the individual scale divisions do not have the same distance from each other, but have a decreasing distance with increasing numerical value.

In operation of the light-beam localizer 14, light source 32 of light-beam localizer 14 illuminates the back of template 35 over condenser lens 33, as can be seen from FIG. 3. The openings of the template 35 are reproduced by object lens 34 on the respective image planes 24, 25 and 26. In FIG. 3 is also indicated the path of rays by which two points P1 and P2 are reproduced on central image plane 24 and the adjoining image planes 25 and 26. It should be noted that the points $P_1'''$ and $P_2'''$ on the underlying plane 26 are displaced to the left, and that points $P_1''$ and $P_2''$ on the overlying plane 25 are displaced to the right with regard to the points $P_1'$ and $P_2'$ on the central plane 24. The numerical values on the scale 37 are so selected that those points of the scale 37 which intersect in the same individual image planes of the axis of symmetry 9 of the radiation diaphragm 8, have a numerical value corresponding to the distance between the focus of the radiation field of the apparatus 3 and the corresponding plane 24, 25 or 26.

Since the individual scale divisions intersect the axis of symmetry 9 of radiation diaphragm 8 in a different angle, as shown in FIG. 2, scale 37 may not be linear, but must be expanded in one direction to a corresponding degree.

If an object, e.g. a patient 10, is introduced lying on a bearing plate 11 into the path of rays, there is, between radiator head 5 and ray trap 7, of the radiotherapy apparatus 3, and the two light-beam localizers 14 facing the top side of the patient 10 are turned on, the top side of patient 10 facing these light-beam localizers 14 will be irradiated with visible light. As it can be seen from FIGS. 1 and 2, the light fans 21, 22 of these two light-beam localizers 14 intersect at that point of the skin surface of the patient 10 which lies on the axis of symmetry 9 of radiation diaphragm 8. This is the point on the skin surface which would be hit by the central beam with maximum opening of the radiation diaphragm 8.

Scale 37, which is projected by one light-beam localizer 14 along with a light fan, is visible in its entire length on the skin surface of the patient 10. As can be seen from FIG. 3, because of the oblique projection to the axis of symmetry 9 of radiation diaphragm 8, it is displaced in longitudinal direction when the surface 24 extending perpendicularly to the axis of symmetry 9 on which it is projected is displaced toward the radiation source or away from it. By corresponding dimensioning of the scale and/or by corresponding selection of the angle between the axis of symmetry 9 of radiation diaphragm 8 and the light fans 21, 22 of the two light-beam localizers, it can be achieved that the scale value read in the intersection of the two light fans 21, 22 corresponds to the respective focal distance.

By adjusting the radiotherapy apparatus 3 by means of the light-beam localizers 12, 13, 14, the examining physician recognizes on the skin surface of patient 10 the point of impact of the central beam 9. At the same time he can read the scale value, that is, the distance between the focus and the skin surface, in the center of the coordinates, that is, in the intersection of the two light fans 21 and 22. By turning the X-ray apparatus 3 and/or by shifting the bearing plate 11 toward the central beam 9, he can now center the patient 10 and set the focus-skin distance desired for treatment. Since the distance of the focus from the axis of rotation 2 is always known, it can also be determined immediately, by subtracting the two numbers, how far the isocenter 20 is under the skin surface.

It is the great advantage of this light-beam localizer arrangement that no material object, that is, no mirror, for instance, is required in the radiation path between radiation source and patient 10, and that this arrangement is independent of the type of radiation of the radiotherapy apparatus 3. Therefore, accelerated electrons can well be used as radiation for the treatment of patients.

While radiotherapy apparatus described herein constitutes a preferred embodiment of the invention, it is to be understood that the invention is not limited to this precise form, and that a variety of changes may be made therein without departing from the spirit and scope of the invention.

What is claimed is:

1. A radiation emitting apparatus, comprising in combination:
    (a) a radiation source comprising an electron accelerator being adapted to project a beam of radiation along a central axis onto a surface to be irradiated, said radiation being focused at a focal point;
    (b) a first light-beam localizer for emitting a first plane light fan towards said surface;
    (c) a second light-beam localizer for emitting a second plane light fan towards said surface, said second light fan intersecting the first light fan in an intersecting line which coincides with said central axis, whereby said first and second light fans form an intersection of two light lines on said surface; and
    (d) means associated with said first light-beam localizer for projecting a scale towards said surface along with said first light fan, wherein said scale is provided with numerals which indicate in said intersection the distance between said focal point and said surface.

2. The radiation emitting apparatus according to claim 1, wherein said first light-beam localizer comprises lens means and an object plane, and wherein a template for generating said scale is provided in said object plane, said template comprising a slit for forming said first light fan, a plurality of transverse slots for forming divisions of said scale, and numerical data for forming said numerals on said surface indicating the distance between said focal point and said surface.

3. The radiation emitting apparatus according to claim 2, wherein said transverse slots have a decreasing distance from each other along said slit.

4. The radiation emitting apparatus according to claim 2, wherein said numerical data in said template are distorted such that they are corrected by the projection on a plane extending perpendicularly to said central axis.

5. The radiation emitting apparatus according to claim 4, wherein said numeral data to be projected are distorted in the object plane in a wedge-shaped manner in such a way that the side closer to said plane extending perpendicularly to said central axis is enlarged in the object plane, while the side of said numeral data farther away from said plane extending perpendicularly to said central axis is reduced in the object plane.

* * * * *